United States Patent
Peters et al.

(10) Patent No.: US 11,823,793 B2
(45) Date of Patent: Nov. 21, 2023

(54) PARTS CO-REPLACEMENT RECOMMENDATION SYSTEM FOR FIELD SERVICING OF MEDICAL IMAGING SYSTEMS

(71) Applicant: KONINKLIJKE PHILIPS N.V., Eindhoven (NL)

(72) Inventors: Marc Andre Peters, Veldhoven (NL); Johannes Henricus Maria Korst, Eindhoven (NL); Serverius Petrus Paulus Pronk, Vught (NL); Mauro Barbieri, Eindhoven (NL); Qi Gao, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 530 days.

(21) Appl. No.: 15/734,258

(22) PCT Filed: Jun. 18, 2019

(86) PCT No.: PCT/EP2019/065944
§ 371 (c)(1),
(2) Date: Dec. 2, 2020

(87) PCT Pub. No.: WO2019/243291
PCT Pub. Date: Dec. 26, 2019

(65) Prior Publication Data
US 2021/0217517 A1    Jul. 15, 2021

Related U.S. Application Data

(60) Provisional application No. 62/686,235, filed on Jun. 18, 2018.

(51) Int. Cl.
G16H 40/40    (2018.01)
G16H 10/40    (2018.01)
(Continued)

(52) U.S. Cl.
CPC .............. *G16H 10/40* (2018.01); *G06Q 10/00* (2013.01); *G06Q 10/06* (2013.01); *G06Q 10/08* (2013.01)

(58) Field of Classification Search
CPC ........ G16H 40/40; G06Q 10/00; G06Q 10/06; G06Q 10/08
See application file for complete search history.

(56) References Cited

U.S. PATENT DOCUMENTS 6,487,479 B1 * 11/2002 Nelson ................. G06Q 10/087
701/34.4
8,271,233 B2 * 9/2012 Butler ..................... F01D 21/20
702/186

(Continued)

OTHER PUBLICATIONS

International Search Report and Written Opinion dated Oct. 7, 2019 for International Application No. PCT/EP2019/065944 Filed Jun. 18, 2019.

(Continued)

*Primary Examiner* — Ramesh B Patel (57) ABSTRACT

At a service device (102), a user interface (106) is provided via which a user submits an order request (117) to order a requested part (X) via the at least one user input device (103). Co-replacement information (116) for the requested part (X) is identified using a co-replacements database (114), and is displayed on the display. For example, a second part (Y) commonly co-replaced with requested part (X) may be identified and recommended for replacement with part (X); or, if two parts (X) and (Y) are ordered then the co-replacement information may be to recommend ordering only one of these parts. At a server hosting the database (114), the order request is received from a service device and the co-replacement information (116) for the requested part is generated using the co-replacements database (114), and the co-replacement information is sent to the service device.

28 Claims, 3 Drawing Sheets

(51) Int. Cl.
*G06Q 10/00* (2023.01)
*G06Q 10/08* (2023.01)
*G06Q 10/06* (2023.01)

(56) References Cited

U.S. PATENT DOCUMENTS

| | | | | |
|---|---|---|---|---|
| 10,510,061 | B2* | 12/2019 | Chan | G06Q 20/326 |
| 10,803,200 | B2* | 10/2020 | Barday | G06F 16/1734 |
| 10,803,202 | B2* | 10/2020 | Brannon | G06F 21/6245 |
| 10,878,127 | B2* | 12/2020 | Brannon | G06F 21/33 |
| 10,944,725 | B2* | 3/2021 | Gunasingam | G06F 16/214 |
| 2002/0103583 | A1* | 8/2002 | Ohmura | G07C 5/008 |
| | | | | 701/31.4 |
| 2004/0024659 | A1* | 2/2004 | Mathew | G06F 11/0793 |
| | | | | 705/28 |
| 2004/0176868 | A1* | 9/2004 | Haga | G05B 19/418 |
| | | | | 700/121 |
| 2004/0199545 | A1* | 10/2004 | Wagner | B65F 1/1638 |
| 2008/0059120 | A1* | 3/2008 | Xiao | G06F 11/0748 |
| | | | | 702/187 |
| 2009/0138139 | A1* | 5/2009 | Tsai | G06Q 10/06 |
| | | | | 705/26.1 |
| 2014/0157054 | A1* | 6/2014 | Yoon | G06F 11/0751 |
| | | | | 714/33 |
| 2015/0052241 | A1* | 2/2015 | Walker | H04L 43/08 |
| | | | | 709/224 |
| 2015/0134400 | A1* | 5/2015 | Kashi | G06Q 10/20 |
| | | | | 705/28 |
| 2017/0032334 | A1* | 2/2017 | Martinez | G06Q 10/20 |
| 2019/0236558 | A1* | 8/2019 | Miles | G06Q 20/02 |
| 2020/0177677 | A1* | 6/2020 | Yang | H04L 67/51 |
| 2023/0214925 | A1* | 7/2023 | Cella | G06Q 20/367 |
| | | | | 705/37 |

OTHER PUBLICATIONS

Appleseed: "6 Use Cases for Compatibility Databases on E-Commerce Sites" Baymard Institute, Oct. 6, 2015.

Moharana, et al: "Determination of optimal kit for spare parts using association rule mining", International Journal of System Assurance Engineering and Management, Springer India, India, vol. 6, No. 3, Jun. 17, 2014.

Cinicioglu, et al: "A framework for automated association mining over multiple databases", Innovations in Intelligent Systems and Applications (INISTA), 2011 International Symposium on, IEEE, Jun. 15, 2011.

* cited by examiner

PARTS CO-REPLACEMENT RECOMMENDATION SYSTEM FOR FIELD SERVICING OF MEDICAL IMAGING SYSTEMS

CROSS REFERENCE TO RELATED APPLICATIONS

This application is the U.S. National Phase application under 35 U.S.C. § 371 of International Application No. PCT/EP2019/065944 filed Jun. 18, 2019, which claims the benefit of U.S. Provisional Patent Application No. 62/686,235 filed Jun. 18, 2018. These applications are hereby incorporated by reference herein.

FIELD

The following relates generally to medical imaging device servicing arts, part replacement ordering systems, and related arts.

BACKGROUND

Occasionally, medical imaging systems experience failures that require servicing. In existing field serving of medical equipment, a remote service engineer (RSE) assesses a system issue by evaluation of the system's log files and customer complaint or a field service engineer (FSE) performs a first visit to the customer site during which the problem is assessed. In many cases the RSE or FSE will decide that one or more components should be replaced. In situations involving a RSE, the FSE can bring along any parts recommended by the RSE to the site during a first visit in an attempt to quickly solve the issue. In cases where the RSE is absent or does not recommend a part, during this first visit, the FSE employs a parts ordering application running on a notebook computer to place an order for the replacement part or parts, with the customer site as the delivery address. In a second visit, the FSE installs one or more of the shipped replacement parts and evaluates whether the problem has been solved. If not, a different replacement part may be installed, possibly without removing the first replacement part. If both replacement parts were ordered during the first visit, complete installation of both parts can be done in a single (second) visit. On the other hand, if only one replacement part was ordered, then the second (different) replacement part must be ordered during the second visit thereby requiring yet a third visit to install that second replacement part.

In some scenarios, both the first and second replacement parts are ordered during the first visit, but the second replacement part is not needed because installation of the first replacement part solves the problem. In other scenarios, first and second replacement parts are ordered during the first visit and installation of the first part fails to solve the problem but the installation of the second replacement part does solve the problem. These various scenarios present statistical tradeoffs between various potential inefficiencies and/or extra cost, e.g. the cost of a third visit versus the cost of delivery and return of an unused second part versus the cost of unnecessarily installing the first part and so forth.

Currently all service work order information is stored in large databases. Experts can go through specific service work order information, or search the database for records filtered on models, specific machines, countries, or periods in time. In this way it is difficult to get an entire understanding of similar situations occurring in different machine types. Thus, it is up to the expert and what he/she recognizes from other situations. Service engineers work under high pressure to get a system back up and running, and therefore are tempted to order and bring multiple parts to the site or replace several parts simultaneously without being sure which one is actually malfunctioning. This is especially the case if they have replaced a first part and found out that that does not solve the issue they will next try to replace a second part. If they find out that this solves the issue, they will possibly not undo the replacement of the first part.

The following discloses certain improvements.

SUMMARY

In some embodiments disclosed herein, a service device includes a display, at least one user input device and an electronic processor operatively connected with the display and the user input device. The device also includes a non-transitory storage medium storing instructions readable and executable by the electronic processor to perform a parts ordering method. The parts ordering method includes providing a user interface via which a user submits an order request to order a requested part via the at least one user input device. The method then operates by receiving co-replacement information for the requested part from a server that accesses a co-replacements database. This co-replacement information is displaying, on the display.

In some embodiments disclosed herein, a non-transitory storage medium stores instructions readable and executable by an electronic to perform a parts ordering method. The parts ordering method includes providing a user interface via which a user submits an order request to order a requested part via the at least one user input device. The method then operates by identifying co-replacement information for the requested part using a co-replacements database. This co-replacement information is displaying, on the display.

In some embodiments disclosed herein, a parts ordering system includes a server, a co-replacement database and an electronic processor operatively connected with the server and co-replacement database. The parts ordering device further includes a non-transitory storage medium that stores instructions readable and executable by the electronic processer to perform the parts ordering method described above.

One advantage resides in providing cost savings by improved diagnostics, reducing the amount of unused parts, and reducing the number of service trips by a service engineer (SE).

Another advantage resides in automatically providing suggestions to the SE to evaluate and test specific additional parts during the first service call.

Another advantage resides in the ability to identify which parts have a high co-replacement frequency.

Another advantage resides in the ability to provide a suggestion for the order in which multiple parts may be replaced in an effort to solve an issue, thus solving the issue as soon as possible.

Another advantage resides in the shortening repair time and decrease the downtime of a system.

Another advantage resides in providing an improved parts ordering device that provides guidance to the SE.

Another advantage resides in providing an improved user interface for a parts ordering device that reduces user effort by anticipating parts likely to be ordered together and expediting order entry for the (probable) co-ordered part.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Medical devices, such as imaging systems are relatively complex, and with use over time, may experience a fault. Upon discovering a system malfunction or fault, the hospital housing the equipment may initiate a service work order, also known as a service call, with a service provider. In some cases, the service provider is an entity related to the original equipment manufacturer and has established a contractual service relation to the end user hospital.

Upon initiation of a service call, remote diagnosis and resolution may initially be attempted. However, in many cases this is unsuccessful and a field service engineer (FSE) may then travel to the site of the malfunctioning equipment, usually the hospital where the equipment is housed. (The term "field service engineer", or FSE, is merely illustrative nomenclature and these terms are to be understood as broadly encompassing any maintenance person who inspects the imaging device on-site and performs on-site repairs as appropriate, regardless of the particular title or term used to refer to such person). At this time, the FSE will investigate the malfunctioning medical imaging device and determine the root cause of the problem. The FSE will then determine whether one or more parts should be replaced in an effort to resolve the issue, and if so, which part(s).

Figure 1:
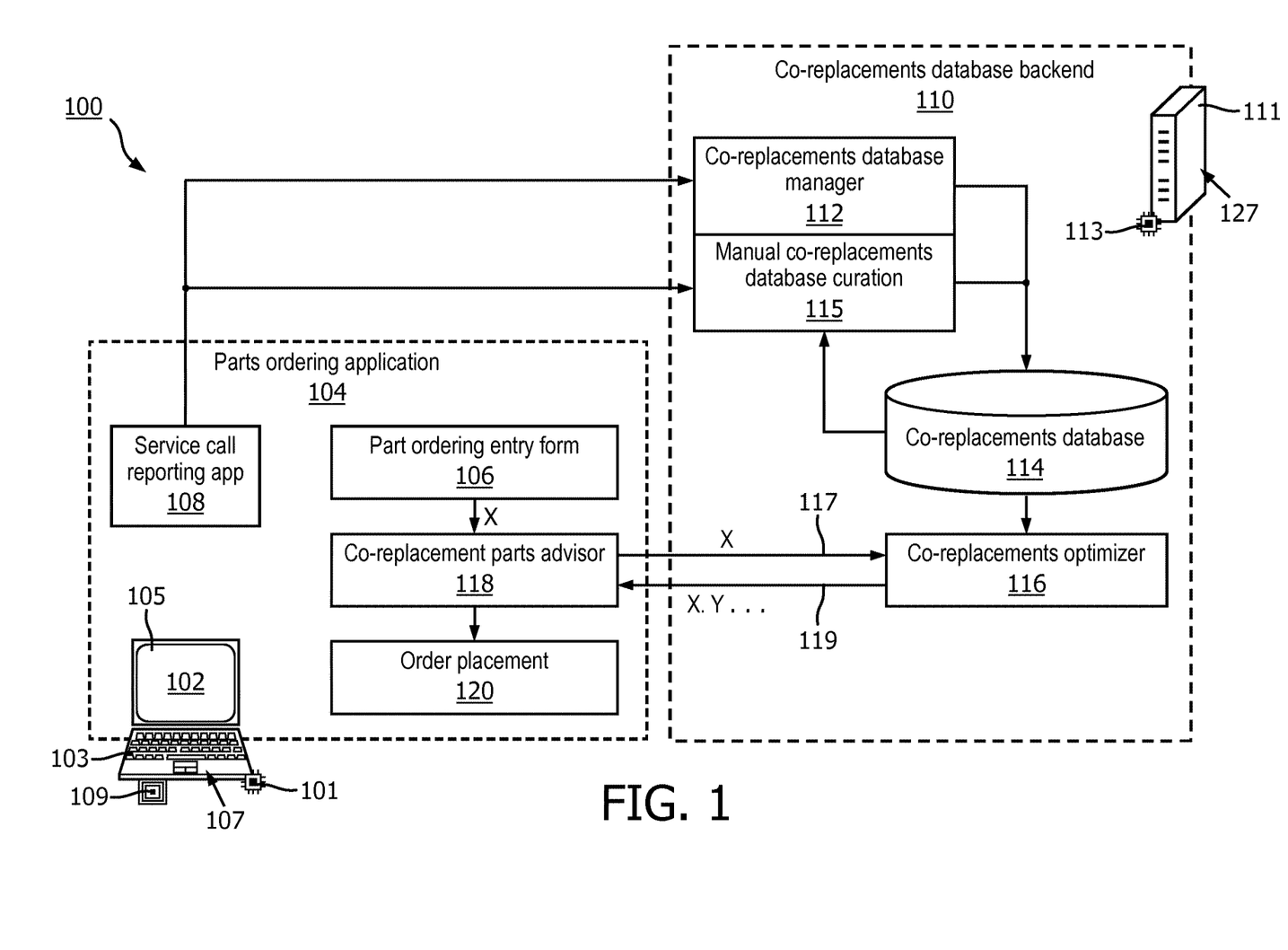
FIG. 1 diagrammatically illustrates a parts ordering system and associated co-replacements database backend in accordance with the present disclosure.

With reference to FIG. 1, a service engineer (SE) generally carries or accesses a service device 102. In some embodiments, the service device 102 is a personal device, such as a mobile computer system such as a laptop or smart device. In other embodiments, the service device 102 may be an imaging system controller or computer integral with or operatively connected with the imaging device undergoing service. As another example, the service device 102 may be a computer located in a call center or other location of an RSE performing initial diagnosis and ordering of parts. The service device 102 is programmed to run a parts ordering application 104 that, among other functionality, provides a parts ordering entry form 106. (The term "service engineer", or SE, is merely illustrative nomenclature and these terms are to be understood as broadly encompassing any maintenance person, such as an FSE or RSE). In other embodiments, the service device may be a mobile device such as a cellular telephone (cellphone) or tablet computer and the parts ordering application 104 may be embodies as an "app" (application program). It is also contemplated for the parts ordering application 104 to be a component of a more comprehensive application, e.g. which includes other components for interfacing with a service log (e.g. illustrative service call reporting application 108) or so forth. The parts ordering application 104 presents a user interface which is displayed on a display 105 associated with the service device 102. The SE may interact with the application via at least one user input device 103 such a mouse, keyboard or touchscreen. The service device further includes an electronic processer 101 and non-transitory storage medium 107 (internal components which are diagrammatically indicated in FIG. 1). The non-transitory storage medium 107 stores instructions which are readable and executable by the electronic processor 101 to implement the parts ordering application 104. The service device may also include a communication interface 109 such that the service engineer may communicate with a backend server 111. Such communication interfaces 109 include, for example, a WiFi or 4G interface or the like for connection to the Internet and/or an intranet. Some aspects of the parts ordering application 104 may also be implemented by cloud processing or other remote processing.

After a determination of the part or parts to be replaced, an SE enters the identification number or code or the like associated with the part (e.g. a part number) requested for ordering into a part ordering entry form 106 in the parts ordering application 104. The SE enters the part number into the entry form 106 via a user input device 103 of the service device 102.

The illustrative parts ordering application 104 includes or interfaces with a service call reporting app 108 (or, alternatively, the service call reporting app 108 could be implemented as a separate program running on the service device 102, e.g. in separate windows or with toggle-based application switching and/or so forth. When the SE visits the site for a requested service call, the SE is typically prompted to communicate reporting information for each visit. The service call reporting app 108 collects data related to the service call, sometimes referred to as service work order data. The reporting information may include identifying information of the malfunctioning equipment such as equipment model and serial numbers that relate to build information. In some embodiments, the service work order data also includes error codes produced by the equipment and logs of equipment use. The service call reporting app also collects information related to the diagnostic and repair information of the equipment including if parts were replaced on the equipment and if replacing those parts has solved to the problem. Often times an SE may make multiple visits to the equipment site for each service call. The service call reporting app may track the history of the servicing done in relation to that particular service call. Once the problem is resolved, a service call related to that issue is considered closed. If a new issue arises, a new service call may be initiated. If the new issue/malfunction is related to a previous service call, the previous service call may be re-opened and updated accordingly.

The information collected from the service call reporting app is typically stored in a service log associated with the medical imaging device being serviced, and may also be uploaded to an archival server maintained by the medical imaging device vendor or other service provider. Additionally, in illustrative FIG. 1, the servicing information collected using the service call reporting app 108 is fed to a co-replacements database backend 110. The backend processing is performed on server 111 equipped with an electronic processor 113 (diagrammatically indicated internal component). The server 111 is equipped with non-transitory storage medium 127 (internal components which are diagrammatically indicated in FIG. 1). While a single server computer is shown, it will be appreciated that the backend 110 may more generally be implemented on a single server computer, or a server cluster, or a cloud computing resource comprising ad hoc-interconnected server computers, or so forth. Co-replacements database manager 112 receives the data from the service call reporting app 108. The co-replacements database manager 112 may then automatically populate and update a co-replacements database 114. The co-replacements database 114 may also be populated or corrected by manual entry of information 115 related to the service call by an FSE, RSE or an engineer of the service provider accessing the backend 110.

The co-replacement database 114 stores information acquired from all service calls. In particular, the co-replacements database 114 stores information of all parts replaced in all service calls. The database may also be updated with information relating to the success (or lack thereof) in resolving an issue by replacing parts. For instance, if a parts "X" and "Y" were replaced and it was later found out that part "Y" was still functional, part "Y" may not have contributed to the success of solving the malfunction issue. In this instance, while part "X" and part "Y" are generally considered co-replacement parts, part "Y" may be disassociated with part "X" in regards to identifying co-replacements parts to be presented to the SE. Thus, a feedback mechanism may be built into the co-replacement optimizer.

When a used part is removed from a machine and replaced with a new part, the used part may be sent to the OEM or the service provider for analysis. The OEM or service provider may run testing on the used part to determine if failure of the used part was a root cause of the equipment malfunction. If the used part was found to be fully functional and not related to the root cause, the co-replacement optimizer and co-replacement database may be updated to disassociate, for that particular service work call, the used part with a co-replaced part.

In some embodiments, the SEs may provide feedback to the co-replacement optimizer and co-replacements data base. If the co-replacement of parts solved the issue, the SE can indicate a positive relationship between a part and co-replacement part. If the co-replacements were not successful in solving the malfunctioning equipment issue the SE may indicate a negative relationship between a part and a co-replacement part. Such resolution information is typically entered into the service log as routine documentation of service calls, and hence may be extracted from the service logs in some embodiments. Extraction of this information may be straightforward if the service call reporting application 108 employs a structured data entry format with constrained fields for entry of resolution information. If more freeform service call logging is used, then keyword searching, natural language processing (NLP), and/or the like may be applied to extract feedback on which part(s) resolved the problem. For example, the text may be parsed into sentences and paragraphs, and a sentence or paragraph containing the part number and a term indicative of success or failure may be identified to extract this information. These are merely illustrative examples.

It is to be appreciated, that the total service work order data contained in the database 114 for each visit of every service call, for all machines that are serviceable, may become quite voluminous. As such, it would be extremely time consuming and inefficient for a person or a team of engineer to sift through the data manually. Moreover, the service device 102 typically is connected via the Internet and may have insufficient communication bandwidth to download the requisite data for performing such manual searching.

The SE's part request 117 via a part number entry into the part ordering form 106 is sent (119) to the co-replacement parts advisor 118. Without loss of generality, the requested part is designated in FIG. 1 as part number "X". The co-replacement parts advisor 118 sends the requested part number "X" to the co-replacement optimizer 116 of the database backend 110. The co-replacements optimizer 116 scans the database 114 to identify one or more other parts that have been co-replaced with the requested part "X" in at least one service call. However, knowing that a part is co-replaced frequently does not tell much, especially if each time the co-replacement was with a different part and/or if many times no additional part was co-replaced. Thus, the co-replacement optimizer 116 may retrieve additional information regarding the frequency that the requested part "X" is replaced with each other co-replacement part in the past (or, in some embodiments, in a specified past time frame, e.g. in the last year. Such a time constraint may be useful to avoid retrieving information on co-replacements that are now obsolete due to new imaging device configurations or so forth). In this regard, a co-replacement percentage may be calculated that relates to how many past service calls the requested part "X" was co-replaced with some other part "Y" in one service work order. In some embodiments, the co-replacement optimizer 116 identifies associated replacement parts that are co-replaced with part "X" in more than T % (said otherwise, in more than a fraction T) of service calls in which the requested part "X" is replaced. In these embodiments, the threshold T may be set either by the SE, or may be hardcoded into the co-replacements optimizer 116 by the service provider that operates the servers 111. For example, the optimizer 116 may generate a list of three parts A, B, and C having a co-replacement percent with part "X" of 40%, 30% and 10%, respectively. In cases where the threshold T is 20%, the co-replacement optimizer 116 would output A and B to the co-replacement parts advisor 118 as parts which are frequently co-replaced with part "X". In this way, only the most relevant and likely replacements for solving the issue will be presented. In some instances, it may be that no parts are identified which are co-replaced with part "X" in at least T % of service calls—in such cases the co-replacement parts advisor 118 does not suggest any parts for ordering together with part "X".

Generally, the service device 102 is connected with the server 110 to place the order for part "X", and hence placing the co-replacements backend 110 at the server is a practical implementation. However, in some embodiments, if the non-transitory storage medium 107 has sufficient capacity then the database 114 and the co-replacements optimizer 116 may be integrated with the parts ordering application 104 at the service device 102. In this way, the service device 102 may then operate offline (i.e. without a connection to the server 111) while still providing co-replacements recommendations.

Other information may be retrieved and associated with the requested part including pricing, shipping costs, and inventory/availability of each co-replacement part. The co-replacement optimizer 116 then sends the retrieved co-replacement information back to the co-replacement parts advisor 118 of the parts ordering application 104. At this time, co-replacement information is displayed on the laptop 105 to the SE. This information may also be taken into account by the co-replacements optimizer 116 in making recommendations of parts to be ordered together with illustrative part "X". For example, the threshold T may be scaled based on the cost of the possible co-replacement part. By way of a more specific example, consider a scenario in which the co-replacements database 114 stores data indicating that statistically a part "A" is co-replaced with the part "X" 15% of the time, while a part "B" is co-replaced with the part "X" 30% of the time. Based on these frequencies alone, the optimizer 116 might recommend ordering part "B" with part "X" but not part "A". However, if part "B" is a heavy and/or bulky part with a high shipping cost; whereas, part "A" is a smaller, lighter part with a very low shipping cost, then the optimizer 116 may recommend ordering part "A" with part "X" but not part "B", due to the low cost of shipping part "A" compared with the high cost of shipping part "B". Other information that may be available in the database 114 can be similarly accounted for, such as part cost, whether a part is already in the inventory, and/or so forth. The shipping costs optimization can also look at other factors, such as the likely return shipping cost of parts that may require return (possibly further scaled by the return rate of the part). The cost analysis can also look at other aspects for scaling the threshold T and/or prioritization besides shipping costs, such as: the location of the FSE compared with the location of the equipment (e.g. is it a five hour drive to get there); schedule of the FSE, both in terms of available time and scheduled location; the additional time required to replace both the requested part and the co-replacement part (compared with the time to replace only the requested part); contractual considerations such as bears the risk of additional cost (customer or supplier); or so forth. In some cost analysis embodiments, thresholds and/or priorities may change given the overall cost analysis.

In some embodiments, either the co-replacement optimizer 116 or the co-replacement parts advisor 118 may rank potential candidates for current co-replacement with the requested part. This means that a part that was co-replaced with the requested part 40% of the time would be ranked higher and potentially listed before a part that was co-replaced with the requested part only 15% of the time (the ranking in this example is based on co-replacement frequencies alone). In some embodiments, the ranking orders the parts list in relation to the co-replacement percentage.

In other embodiments, the ranking orders the parts listing in relation to cost effectiveness, thus taking into account the shipping and/or part pricing. For example, small easy to ship parts that are inexpensive may be ranked and listed before parts that are large, bulky, and expensive. In this way, the co-replacement optimizer 116 and part advisor 118 may suggest the least expensive route to potentially resolve the issue.

Presenting the list of potential current co-replacements to the SE may suggest to the SE additional components of the malfunction machine to check. For example, the SE may request part "X" and the co-replacement optimizer 116 may identify a part "Y" is co-replaced with the requested part 30% of the time. This provides a suggestion to the SE that additional diagnostic testing focused on part "Y" may provide insight to the malfunctioning of the system. In fact, it may be determined that the root cause of the issue was with part "Y" rather than with part "X" or potentially that both parts "X" and "Y" may need to be replaced.

In some embodiments, the co-replacement parts optimizer 116 and parts advisor 118 may relate to preventative maintenance. Here, the co-replacement optimizer 116 may suggest replacing a routine maintenance item, part "Y", along with replacement of the requested part "X". Generally, a routine maintenance part may need to be replaced periodically. However, replacement of part "X" may provide easy access to part "Y" and thus it may be cost effective to replace both parts "X" and "Y" at the same time to reduce the number of trips or time that an SE would spend performing routine maintenance later on. Advantageously, such co-replacement of parts based on preventative maintenance considerations will be automatically reflected in the statistics of the empirical database 114. The optimization of part co-replacement for purpose of preventative maintenance preferably also takes into account the remaining likely useful life of the currently installed part "Y", and thus its value, so as to avoid unnecessarily early replacement of a part that still has a long remaining useful life. The optimization may also take into account other factors, such as the additional downtime to replace part "Y" in the above example added to the downtime already required to replace part "X". For example, if the downtime for replacing part "X" is already strongly adversely impacting the customer, then the additional downtime to further replace routine maintenance item "Y" may be unwarranted. This can be quantified, for example, by an escalating (e.g. exponential) penalty for longer total downtime.

Figure 2:
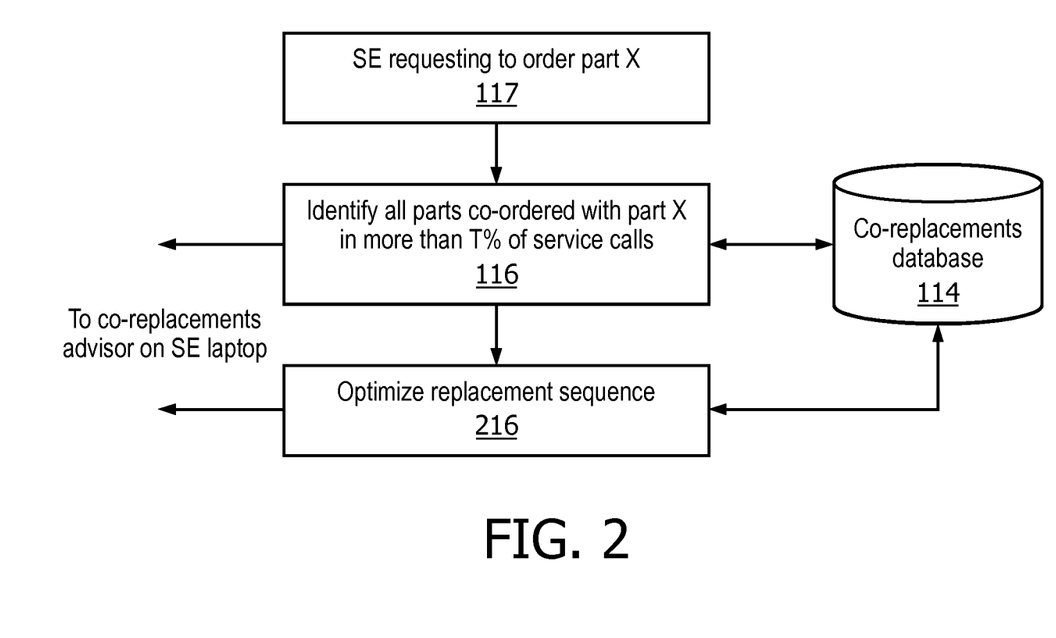
FIG. 2 diagrammatically illustrates operation of the illustrative co-replacements database manager of FIG. 1 to provide a recommendation to order a second part.

In some embodiments and with reference to FIG. 2, a replacement sequence may be calculated and sent to the co-replacement advisor 118. Here, a request for the order of a part "X" 117 is sent to the co-replacement part optimizer 116. The co-replacement optimizer 116 scans the co-replacement database 114 to determine and generate a list all parts co-ordered with the requested part "X" at a frequency of higher than threshold T % of service calls. In an optional step 216, if two parts (e.g. "X" and "Y") are co-replaced more frequently than T % of the time, then the order of replacement for the parts "X" and "Y" is optimized at 216 to determine a replacement sequence. The optimized replacement sequence is the sequence/order in which multiple parts should be replaced that is statistically most likely to resolve the problem efficiently (as measured in time, total cost, or another suitable efficiency metric). In the foregoing example, the possible sequences are: (1) replace "X" first followed by "Y" if the problem persists; (2) replace "Y" first followed by "X" if the problem persists; or (3) replace both "X" and "Y" together before evaluating whether the problem has been resolved. (In some embodiments or situations, sequence (3) may not be considered as an option). The choice of optimal sequence can be based on solving the issue as soon as possible or it can be driven by cost arguments, or can be based on some weighted combination of these considerations. Thus, a part that is relatively cheap could be replaced first before a more expensive part is to be replaced.

In the following, some quantitative approaches for choosing the replacement order are described. For a pair of parts p (part "X") and p' (part "Y") that are often co-replaced, the probability $P(p)$, $P(p')$, and $P(p+p')$, denoting the probability that only p, only p', or both p and p' have to be replaced to resolve the issue, is known. Knowing the probability, the sequence in which the parts have to be replaced in an effort to resolve the issue can be determined. Here, $T(p)$, $(p')$, $T(p \rightarrow p')$ and $T(p' \rightarrow p)$ denote the times that are involved in replacing only p, only p', p before p' and p' before p, respectively. These parameters can then be used to determine the best order of replacement.

One can use the rule to select a part p as the part that is to be replaced first, whenever the corresponding expected total replace time is smallest. The corresponding expected total replacement time (i.e. expectation) is given by Equation 1.

$$E_{p\,first}(T) = P(p) \cdot T(p) + P(p') \cdot T(p \rightarrow p') + P(p+p') \cdot T(p \rightarrow p') \quad \text{Equation 1}$$

This can be rewritten as Equation 2.

$$E_{p\,first}(T) = P(p) \cdot T(p) + (1-P(p)) \cdot T(p \rightarrow p') \quad \text{Equation 2}$$

Similarly, the expected total replacement when p' is replaced first is given by Equation 3.

$$E_{p'\,first}(T) = P(p') \cdot T(p') + (1-P(p')) \cdot T(p' \rightarrow p) \quad \text{Equation 3}$$

In the example of FIG. 2, the co-replacement parts advisor is employed in response to the SE ordering a single part "X", in order to determine whether it should be recommended to additionally order some other part "Y" based on co-replacement frequencies, total time and/or cost, or another efficiency metric. In other contemplated applications, the co-replacement parts advisor may be employed in a context where the SE is placing an order for two parts (designated, again without loss of generality, as parts "X" and "Y") in order to provide a recommendation not to order one of these parts. In a variant embodiment, the recommendation could be to perform some discriminating test to decide which of parts "X" and "Y" to order alone, rather than incurring the time and cost involved in ordering both parts "X' and "Y" together.

Figure 3:
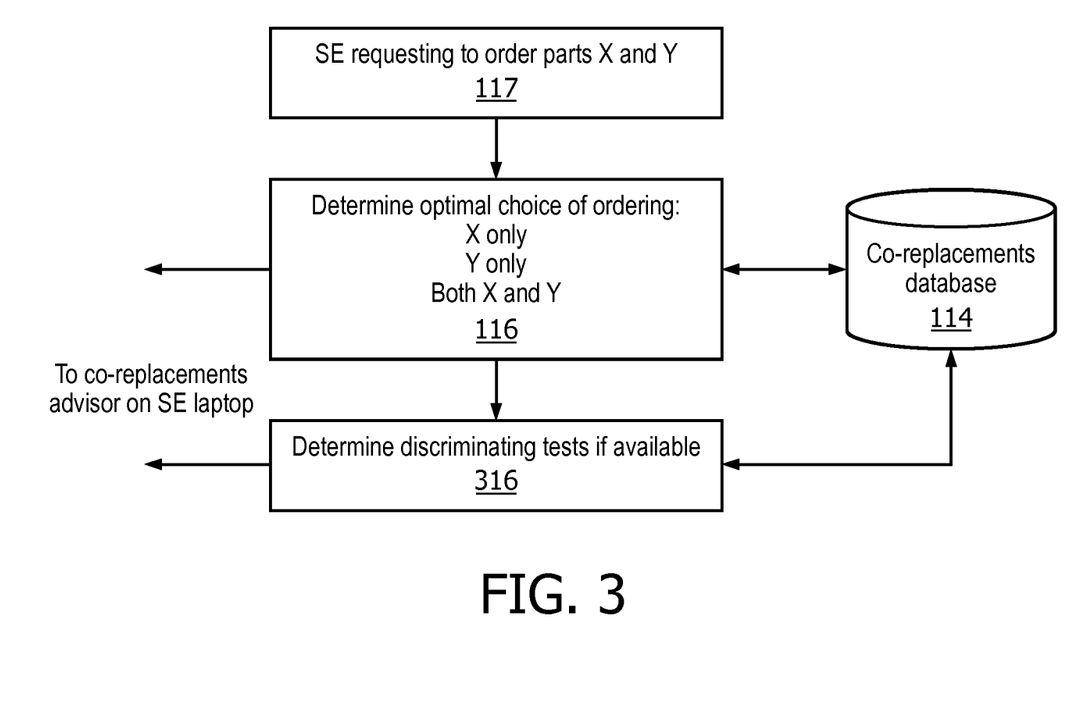
FIG. 3 diagrammatically illustrates operation of the illustrative co-replacements database manager of FIG. 1 to provide advice when two parts are ordered together.

Thus, in some embodiments and with reference to FIG. 3, the co-replacement optimizer 116 may evaluate a decision by a SE to replace multiple parts. Here, a request for the order of multiple parts "X" and "Y" 117 entered into the order form 106 is sent to the co-replacement part optimizer 116. The co-replacement optimizer 116 scans the co-replacement database 114 to determine and generate an optimal choice for ordering only part "X", only part "Y", or ordering both "X" and "Y". For example, the database 114 may be scanned to identify all instances (e.g. service calls) in which only part "X" was ordered, only part "Y" was ordered, or both parts "X" and "Y" were ordered, to determine which part most often resolved the problem (i.e. resolved the service call). For example, if installing part "X" solved the problem 90% of the time and installing part "Y" solved the problem only "7%" of the time, the recommendation may be to consider ordering only part "X" at this time. Again, factors other than resolution frequency may be taken into account, e.g. shipping costs of the respective parts "X" and "Y" and/or so forth. Additionally or alternatively, the optimizer 116 may determine at 316 if discriminating tests are available to the SE to provide additional insight into the actual required parts to resolve the malfunction issue. These tests would generally need to be manually annotated to the co-replacements database 114, although it is alternatively contemplated to employ NLP, keyword searching or the like applied to the service logs to learn commonly employed discriminating tests for a given context (e.g. given problem and the ordering of parts "X" and/or "Y") automatically. A ranking according to the optimal choice of parts as well as notification of available testing is presented to the SE via the co-replacement parts advisor 118. The co-replacement parts advisor 118 may also escalate the advising process to a human specialist when appropriate. For example, if the order in question is large (e.g., as measured by cost of parts, number of parts, and/or so forth), or is being made in conjunction with a second (or third, or other chosen threshold) service call back, then the order processing may be escalated to a specialist for consultation to help determine if co-replacement should be shipped as recommended by the co-replacement parts advisor 118 and/or as being entered by the SE, or should be modified. In this case, the co-replacement information that is generated and sent includes an identification of an escalation condition indicative of a large order, and the resulting displayed co-replacement information may include, for example, display of a user interface dialog with the specialist.

Returning to FIG. 1, an actual order placement 120 leveraging the co-replacement recommendations from the advisor 118 may be variously implemented. In some embodiments, an SE reviews the recommendation(s) provided by the co-replacement parts advisor 118, and if the SE agrees with the recommendation this agreement is indicated via the user input device 103 and an order for the originally requested part "X" and any additional recommended co-replacement parts is automatically placed at the operation 120. This approach increases user interfacing efficiency as the order for the additionally recommended parts is automated, reducing the amount of data that needs to be input by the SE (for example, the part number for a recommended co-replacement part "Y" does not need to be entered). In other embodiments, the co-replacement part "Y" is suggested by the co-replacement parts advisor 118 but the actual order is manually placed at operation 120 by the SE. In yet other embodiments, some intermediate approach may be used, e.g. upon agreement by the SE with the recommendation to order co-replacement part "Y" a second instance of the order entry form 106 may be presented with information such as the part number for part "Y" automatically populated into the form. Such an intermediate approach still increases user interfacing efficiency to a substantial degree, while ensuring the SE retains full control of the ordering process.

In some embodiments, an order will not be placed until the SE has entered a confirmation of inspection of the parts in the malfunctioning machine corresponding to the suggested co-replacement part. The confirmation may be entered by satisfying conditions presented by the user interface such as an affirmative click in a dialog box of the parts ordering application. In this way, a suggested co-replacement part may not be ordered if the SE determines through testing that the suggested co-replacement part is correctly functioning.

In some embodiments, the co-replacements optimizer 116 may identify groups of parts that are co-replaced frequently. This can be groups of 3, 4, or more parts. These groups of parts being co-replaced may be linked to common issues with specific products.

In some embodiments, the database may include replace-by-chain data. That is multiple parts with different identification numbers may be considered one as one replacement part. The replace-by-chain specifies a sequence of parts, $P_1$, $P_2$, . . . , $P_n$ that can be considered as successive version of the same functional part. Assuming that no older parts than $P_n$ will be in stock, the replacement of any of $P_1$, $P_2$, . . . , $P_n$, will result in ordering $P_n$. For determining replacement statistics $P_1$, . . . , $P_n$ can be considered as the same part, such that a replacement of $P_1$ and "Y" and another replacement of $P_2$ and "Y" are actually two instantiations of the same co-replacement.

A non-transitory storage medium includes any medium for storing or transmitting information in a form readable by a machine (e.g., a computer). For instance, a machine-readable medium includes read only memory ("ROM"), solid state drive (SSD), flash memory, or other electronic storage medium; a hard disk drive, RAID array, or other magnetic disk storage media; an optical disk or other optical storage media; or so forth.

The methods illustrated throughout the specification, may be implemented as instructions stored on a non-transitory storage medium and read and executed by a computer or other electronic processor.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A service device comprising:
a display;
at least one user input device;
an electronic processor operatively connected with the display and the at least one user input device; and
a non-transitory storage medium storing instructions readable and executable by the electronic processor to perform a parts ordering method including:
providing a user interface via which a user submits an order request to order a requested part via the at least one user input device;
receiving co-replacement information for the requested part from a server that accesses a co-replacements database;
displaying, on the display, the co-replacement information.

2. The service device of claim 1 wherein:
the receiving of co-replacement information for the requested part includes receiving an identification of a second part associated with the requested part, and
the displaying includes recommending co-ordering the second part together with the requested part.

3. The service device of claim 2 wherein the parts ordering method further includes:
via the user interface, updating the order request to include the requested part and the second part; and
placing the updated order request including transmitting the updated order request to an ordering system via a communication interface.

4. The service device of claim 1 wherein the requested part includes a first requested part and second requested part and the receiving of co-replacement information includes receiving an identification of one of the first requested part or the second requested part, and the displaying includes recommending ordering only the identified one of the first requested part or the second requested part.

5. The service device of claim 4 wherein the parts ordering method further includes:
via the user interface, updating the order request to include only the identified one of the first requested part or the second requested part; and
placing the updated order request including transmitting the updated order request to an ordering system via a communication interface.

6. The service device of claim 1 wherein the co-replacement database is populated with service work order data and the parts ordering method further comprises:
entering service work order information into the user interface; and
sending the entered service work order information to a database manager of a remote server, wherein the database manager automatically populates and updates the co-replacement database with the entered service work order information.

7. The service device of claim 1 wherein the received co-replacement information includes identification of a co-replacement part associated with the requested part and the service device is further configured to perform a diagnostic suggestion method including:
providing a notification via the display to check the condition of the identified co-replacement part.

8. The service device of claim 7, wherein the diagnostic suggestion method includes presenting available testing to the display.

9. The service device of claim 1 wherein the received co-replacement information includes identification of at least one additional part associated with the requested part and a suggested replacement sequence for the requested part and the at least one additional part, and the displaying includes displaying the suggested replacement sequence.

10. The service device of claim 1 wherein the service device comprises a mobile computer, a cellular telephone, a call center computer, or an imaging system controller or computer integral with or operatively connected with an imaging device.

11. A non-transitory storage medium storing:
service work order data including at least a database of parts that have been replaced during at least one service call; and,
instructions readable and executable by an electronic processor to perform a co-replacement optimization method comprising:
receiving an order request from a service device including a request for replacement part;
generating co-replacement information for the requested part using the co-replacements database;
sending the co-replacement information for the requested part to the service device.

12. The non-transitory storage medium of claim 11 wherein:
generating co-replacement information for the requested part includes identifying a second part associated with the requested part, and
sending the co-replacement information includes recommending co-ordering the second part together with the requested part.

13. The non-transitory storage medium of claim 12 wherein the identifying of the second part associated with the requested part is based at least on a fraction of times the additional part is replaced together with the requested part in the co-replacements database exceeding a threshold.

14. The non-transitory storage medium of claim 13 wherein the threshold is used in identifying the second part is scaled based on additional factors including at least a shipping cost of the second part.

15. The non-transitory storage medium of claim 11 wherein the requested part includes a first requested part and a second requested part and the generating of co-replacement information includes identifying one of the first requested part or the second requested part, and the sending the co-replacement information includes sending a recommendation to order only the identified one of the first requested part or the second requested part.

16. The non-transitory storage medium of claim 15 wherein the identifying of one of the first requested part or the second requested part is based on data in the co-replacements database on which requested part most often resolved an associated service call.

17. The non-transitory storage medium of claim 11, wherein the co-replacement optimization method further comprises:

subsequent to sending the co-replacement information, receiving service work order data from the service device and updating the database with information on parts that have been replaced according to the received service work order data.

18. The non-transitory storage medium of claim 11 wherein the co-replacement optimization method further comprises suggesting a replacement sequence wherein the replacement sequence is the sequence in which part "X" and part "Y" should be replaced that is statistically most likely to resolve the problem efficiently, wherein the replacement sequence is determined by calculating expectations ($E_{X\,first}$) and ($E_{Y\,first}$) for an efficiency metric comprising total replacement time based on the probabilities P(X) that only part "X" needs to be replaced and P(Y) that only part "Y" (P(Y)) needs to be replaced and further based on replacement times including time T(X) for replacing only part "X", time T(Y) for replacing only part "Y", time T(X→Y) for replacing part "X" and then part "Y", and time T(Y→X) for replacing part "Y" and then part "X".

19. The non-transitory storage medium of claim 11 wherein:
generating co-replacement information for the requested part includes identifying a preventative maintenance part that is replaced periodically and is more easily accessed during replacement of the requested part, and
sending the co-replacement information includes recommending co-ordering the preventative maintenance part together with the requested part.

20. A parts ordering system comprising:
a non-transitory storage medium as set forth in claim 11; and
a server including an electronic processor operatively connected with the non-transitory storage medium to perform the co-replacement optimization method.

21. The parts ordering system according to claim 20, wherein the co-replacement database is populated with service work order data received from at least one service device, the populating being performed by one of a database manager and manual service engineer input into the co-replacement database.

22. A co-replacement optimization method comprising:
maintaining a co-replacements database for service calls pertaining to medical imaging systems including at least identification of parts that have been replaced during service calls;
receiving an order request at a server for a requested part;
generating co-replacement information for the requested part using the co-replacements database; and
replying to the order request by sending the co-replacement information.

23. The co-replacement optimization method of claim 22 further comprising:
generating the order request at a service device and transmitting the order request to the server;
receiving the co-replacement information sent by the server at the service device; and
displaying the co-replacement information at the service device.

24. The co-replacement optimization method of claim 23 wherein:
generating co-replacement information for the requested part includes identifying an escalation condition defined by a metric indicative of the order request being a large order request, and
displaying the co-replacement information at the service device includes displaying a user interface dialog with a specialist.

25. The co-replacement optimization method of claim 22 wherein the co-replacement information comprises:
an identification of an additional part recommended to be co-replaced with the requested part based at least on a fraction of times the additional part is replaced together with the requested part in the co-replacements database.

26. The co-replacement optimization method of claim 25 wherein the identifying of the additional part recommended to be co-replaced with the requested part is based at least on a fraction of times the additional part is replaced together with the requested part in the co-replacements database exceeding a threshold.

27. The co-replacement optimization method of claim 26 wherein the threshold is used in identifying the additional part is scaled based on one or more of a cost of the additional part, a shipping cost of the additional part, and a return rate of the additional part.

28. The co-replacement optimization method of claim 22 wherein the co-replacement information comprises:
a recommendation to order one requested part out of at least two requested parts wherein the recommendation is based at least on the fraction of times each respective requested part resolves a corresponding service call as indicated in the co-replacements data base.

\* \* \* \* \*